(12) United States Patent
Mills, Jr.

(10) Patent No.: US 6,284,883 B1
(45) Date of Patent: Sep. 4, 2001

(54) DNA AFFINITY CHROMATOGRAPHY

(75) Inventor: Allen Paine Mills, Jr., Chatham, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/739,010

(22) Filed: Dec. 19, 2000

(51) Int. Cl.$^7$ .................................................... C07H 21/00
(52) U.S. Cl. ................................................................ 536/25.4
(58) Field of Search ............................. 536/25.4; 476/94; 435/6

(56) References Cited

PUBLICATIONS

Jarrett, J. Chromatography, vol. 618 (1993) pp. 315–339.*

\* cited by examiner

*Primary Examiner*—James Ketter

(57) ABSTRACT

The invention is a method for separating target oligomers that are nucleic acid oligomers or analogs of a nucleic acid oligomer having a desired first subunit sequence, from impurity oligomers that is do not comprise the first subunit sequence. According to the invention, a mixture of oligomers comprising the target oligomers and the impurity oligomers, are loaded onto a separation medium under conditions such that the mixture of oligomers physically moves through the separation medium. The separation medium contains separation oligomers comprising a subunit sequence that is complementary to the first subunit sequence, and the separation oligomers are distributed in the separation medium during movement of the target and impurity oligomers through the separation medium. Conditions are controlled so that the rates of hybridization and dissociation of complementary portions of the target oligomers and the separation oligomers in the separation medium are about the same. The mixture of oligomers is allowed to move through the separation medium until the target oligomers are separated from the impurity oligomers.

22 Claims, 2 Drawing Sheets

DNA AFFINITY CHROMATOGRAPHY

BACKGROUND OF THE INVENTION

1. Field of the Invention

This invention relates to a method for purifying DNA and RNA oligonucleotides and analogs thereof.

2. Background

DNA oligomers containing a few to on the of order 100 bases are commonly produced by automatic synthesizer machines and are available from many commercial suppliers. Oligomers are formed by adding the DNA bases one at a time by chemical modification of the ends of the growing oligomers. The steps in this process are not 100% efficient, and the resulting oligomeric products typically have errors of base omission of a fraction of a percent per base. There may also be errors of base substitution or addition that are dependent on chemical purity. Hence, significant impurities will be present in the form of shortened and base-substituted oligomers. While there may be a significant number of oligomers containing errors, the quantity of oligomers having any particular incorrect sequence is very small. The present state of the art requires purification using columns or electrophoresis gels to attain 95% purity.

Mosaic Technologies offers a gel supported DNA product that is capable of carrying out this type of purification. However, the gel operates by immobilizing the desired DNA by capture on DNA adhered to the gel having complementary sequences and subsequently removing the desired DNA from the gel as a purified product.

SUMMARY OF THE INVENTION

In one aspect, the invention provides a method of separating target DNA oligonucleotides, RNA oligonucleotides and analogs thereof from impurity DNA oligonucleotides, RNA oligonucleotides and analogs thereof using affinity chromatography. The method uses a chromatographic material having a separation medium and separation oligomers with a subunit sequence complementary to the desired subunit sequence. The chromatographic separation which may include, for example, column chromatography or electrophoresis, is conducted under conditions wherein the rates of hybridization and dissociation of oligomers having the desired sequence and the separation oligomers is about the same. This may be accomplished by conducting the separation at about the melting temperature of the double stranded complex consisting of the oligomer having the desired sequence and its complement.

In various embodiments, the separation medium may be, for example, an electrophoretic gel or a chromatographic matrix such as beads or fibers that may be loaded into a chromatography column. The separation oligomers may be bound to the separation material or travel with the target oligomers through the separation medium. The method is particularly useful for purifying DNA and isolating DNA oligonucleotides having single nucleotide polymorphisms.

One advantage of some embodiments is a form of DNA affinity chromatography that provides a higher purity than prior art purification processes.

Further objectives and advantages will become apparent from a consideration of the description and examples.

DETAILED DESCRIPTION OF THE EMBODIMENTS

Figure 1:
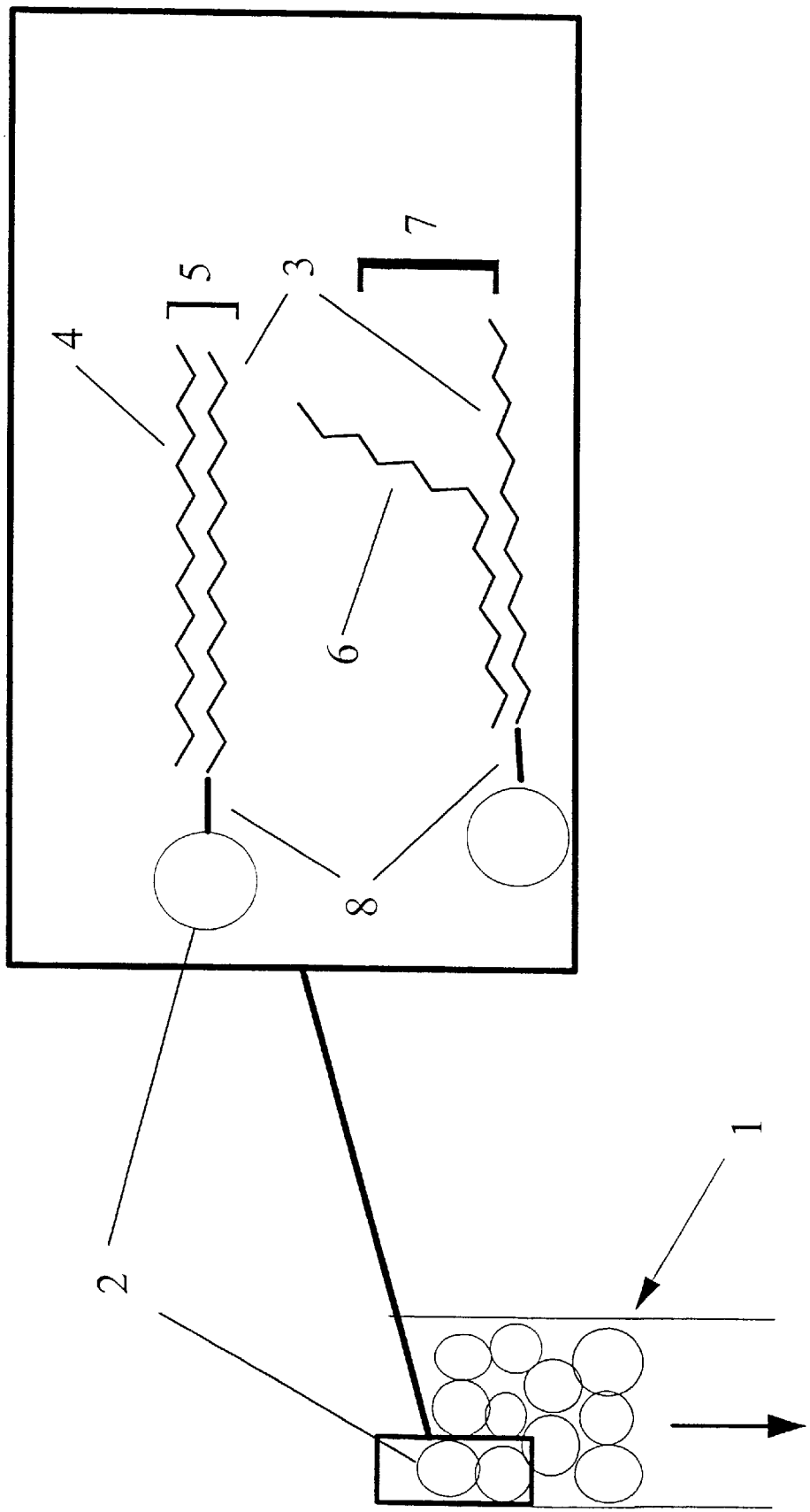
FIG. 1 is a diagram showing an embodiment of the invention having the separation oligomers attached to the separation medium in a column.

In describing embodiments of the present invention, specific terminology is employed for the sake of clarity. However, the invention is not intended to be limited to the specific terminology so selected. All references cited herein are incorporated by reference as if each had been individually incorporated.

Various embodiments purify DNA and analogs produced by automated synthesizers using a simple chromatographic process to provide high purity.

Unlike conventional methods, embodiments include conducting affinity chromatography under conditions where hybridization and dissociation of oligomers and complements occur at nearly equal rates. Use of these conditions has not been previously appreciated, realized or utilized. For DNA oligomers, the present embodiments include conducting the purification at or near the melting temperature of the double stranded DNA complex consisting of the DNA oligomer and its complement.

"Oligomers" refers to RNA or DNA oligonucleotides, RNA or DNA oligonucleotide analogs, or a combination of RNA and/or DNA oligonucleotides and RNA and/or DNA oligonucleotide analogs. The RNA or DNA oligonucleotide analogs employed for the present invention can be oligomers in which from one to all nucleotide subunits are replaced with a nucleotide analog to confer desired properties such as increased detectability, increased hybridization affinity, and resistance to degradation by a nuclease. Such oligonucleotide analogs include but are not limited to oligomers comprising 2'-O-alkyl ribonucleotides, phosphorothioate or methylphosphonate internucleotide linkages, peptide nucleic acid subunits, and nucleotides modified by attachment of radioactive or fluorescent groups, groups which intercalate, cross-link or cleave a nucleic acid, or groups which alter the electric charge or hydrophobicity of the oligomers. Methods for making and using oligonucleotides and oligonucleotide analogs such as those listed above are well known to those skilled in the art of making and using sequencespecific hybridizing oligomers.

In general, an essential characteristic of the target oligomers separable by the method of the invention is that they are able to hybridize specifically to separation oligomers having complementary subunit sequences to form stable double-stranded complexes. The statement that a target oligomer hybridizes specifically to a separation oligomer is intended to mean that at least a portion of a target oligomer comprising a nucleotide sequence complementary to a sequence in a separation oligomer binds by Watson-Crick base-pairing to the complementary portion of the separation oligomer to form a stable double-stranded complex. The binding occurs under hybridization conditions that are sufficiently stringent that impurity oligomer molecules having fewer bases complementary to, or forming less stable duplex structures with, the separation oligomer do not hybridize to the separation oligomer to form stable double-stranded complexes or do so with a rate of hybridization that is significantly less than different from the rate of dissociation. The selection of parameters such as the lengths of the complementary portions of the different oligomers and of the conditions used in hybridization, e.g., the type of oligomer, concentration of oligomer and ionic strength of the solvent, so that the target oligomers hybridize specifically to their complementary separation oligomer counterparts are well known to persons of ordinary skill in the art.

"Affinity chromatography" as used herein is a method in which a sample containing target oligomers and impurity oligomers is allowed to move through a column that contains a separation medium. Separation oligomers are also present and may either be bound to the separation medium or allowed to flow with the sample through the separation medium. In particular, the method of the present invention utilizes separation oligomers in the separation medium that are complementary to the target oligomers.

"Target oligomers" refers to oligomers whose purification is desired. "Impurity oligomers" are those oligomers found in the same sample containing the target oligomers and having a subunit sequence that is different from the subunit sequence of the target oligomers. Impurity oligomers may contain, for example, errors of subunit omission, addition or substitution. "Separation oligomers" are oligomers having a sequence that is complementary to a sequence of at least a portion of the target oligomers. Separation oligomers must be capable of hybridizing specifically with at least a portion of the target oligomers under selected conditions.

"Subunits" are the structural units of an oligomers which bind to complementary subunits during hybridization. For example, for DNA and RNA oligonucleotides, the subunits are either the nucleotides joined together to form the oligomer or the bases attached to backbone of the oligomer.

According to the present method, a separation medium such as a column or gel is activated with separation oligomers which contain a subunit sequence that is both complementary to the at least a portion of the subunit sequence of the target oligomers and is capable of hybridizing with the target oligomers. Exemplary separation media include modified agarose gel, and grains or fibers to which separation oligomers may be attached. During the purification process, a sample, which contains a mixture of target oligomers and impurity oligomers, travels through the separation medium. As the sample travels through the medium, the target oligomers hybridize with and dissociate from the separation oligomers. Ideally, the separation oligomers contain a subunit sequence that is complementary to at least part of the subunit sequence of the target oligomers. But, the present method can be used to purify target oligomers even if the separation oligomers contain amounts of "impurity separation oligomers", i.e. separation oligomers having errors of subunit addition, omission or substitution, on the order of the amount of impurity oligomers in the sample. In order to achieve effective separation, it is necessary that the separation be conducted under conditions where the rate of hybridization and the rate of dissociation of the complementary portions of the target oligomers and the separation oligomers be about the same. Preferably, the ratio of the rate of hybridization to the rate of dissociation is from about 35:65 to about 65:35. At these ratios, from about 35% to about 65% of the target oligomers are hybridized with separation oligomers at any one time. As will be appreciated, the precise range of usable ratios depends on many factors and a wider range may be usable under some conditions for some target oligomers. Ideally, the separation is conducted under conditions where the rate of hybridization is equal to the rate of dissociation. Under this condition, the drift velocity for the target oligomer is $0.5V_0$, where $V_0$ is the drift velocity in the absence of the separation oligomer. Drift velocity refers to the rate of travel of oligomers through the separation material. If the drift velocity for impurity oligomers is about $0.66V_0$, the method will be sufficient to separate the target oligomers from the impurity oligomers.

FIG. 1 is a diagram showing a first embodiment of the invention having the separation oligomer 3 attached to the separation medium 2 in a column 1. Using DNA as an example of a target oligomer, a separation oligomer 3 is attached to an affinity chromatography separation material 2 through a linking unit 8. The separation medium may be, for example, a chromatographic matrix such as beads or fibers or, preferably, an electrophoretic gel. A sample is added to the column 1 and allowed to flow. The separation oligomer 3 is DNA that is complementary to the target DNA oligomer 4 being purified. The separation is conducted at the "melting temperature" of the desired DNA and its complement, i.e. the temperature at which the rates of hybridization and dissociation of perfectly matched target oligomer-separation oligomer pairs 5 are approximately equal. Another way of visualizing this is that the melting temperature is the temperature at which perfectly target DNA-complementary DNA pairs 5 spend half of the time attached together. Impurity oligomers 6 will not bind as effectively to the separation oligomer 3. This lack of effective binding leads to mismatched oligomer-"complementary" oligomer paris 7. Thus, because binding in the impurity oligomer-separation oligomer pair 7 is less effective than binding of target oligomer-separation oligomer pairs 5, the impurity oligomer 6 will dissociate more rapidly from the separation isomer 3 than will target oligomers 4. Although the oligomer pairs 5 and 7 are shown in FIG. 1 to be attached linearly for simplicity, the paris normally form a double helix.

The concept of melting temperature is well known in the art and there are several formulas for estimating melting temperatures, as well as empirical methods of determining melting temperatures. Among the key factors on which melting temperature depends are: the chain length of the oligomer molecule; the type and concentration of ions in the solution, the concentration of the oligomers and the specific sequence of subunits in the oligomer. Persons skilled in the art are familiar with methods for estimating and determining oliogomer melting temperatures that are suitable for practicing the invention.

With reference to FIG. 1, at the melting temperature, impurity oligomer-separation oligomer pairs 7 will spend significantly less time bound together than perfectly matched target oligomer-separation oligomer pairs 5, even if the impurity oligomer 6 and separation oligomer 3 differ by only a single base. Thus, impurity oligomers 6 will thus have a much faster drift velocity in the separation medium 2 relative to the target oligomers 4 at temperatures near the melting temperature. As a result, purified target oligomers 4 are collected as the slowest moving component from the separation column 1. The degree of purity of the target oligomers 4 is very high because the single-base errors are typically distributed throughout the oligomer, i.e. at different locations in the subunit sequences. Hence, little likelihood of finding complementary subunit sequences on the separation oligomers 3 exists, even when the separation oligomers 3 used in the separation medium 2 have single base errors at concentrations comparable to the concentration of subunit errors in the impurity oligomers 6. Since many different pairing possibilities are sampled by an individual separation oligomer 3, only target oligomers 4 will be hybridized multiple times, and thus selected by the separation process. For example, if the original sample contains 50% the target oligomers, and the target oligomer 50 bases in length, each of the possible impurity oligomers with single base errors at a particular position will be present at a concentration level of roughly 1%. Under these conditions, separation may be obtained if the separation oligomer 3 in the column or gel has a comparable impurity concentration level as the impurity level in the sample. If the temperature is adjusted so that about half the time the nominal sequences are bound to their complements and that, under these conditions, sequences differing by a single base or subunit have a dwell time, i.e., will be hybridized to the separation oligomer, about half as long as that of perfectly matched pairs. It will be appreciated that similar results can be obtained by conducting the separation at a particular temperature and adjusting either the sample concentration or ionic strength of the solution to obtain a condition where the rate of hybridization of target oligomers to separation oligomers will be about the same as the rate of dissociation of target oligomer-separation oligomer pairs. The dwell times of impurity oligomers may range from about 35% to about 65% of the dwell the of target oligomers. Thus, the target DNA oligomers will be selectively retarded in movement through the separation medium with respect to the impurity oligomer-separation oligomer pairs.

The principle and subtle difference between the above method and known methods is the operation of the separation column or gel under conditions where the rate of hybridization is about the same as the rate of dissociation for the target oligomer-separation oligomer pairs. This allows the easy elimination of oligomers with single-base mismatches to purified sample. Where the target oligomer is DNA at the melting temperature, the rate of hybridization is about the same as the rate of dissociation of the double stranded complex consisting of the target oligomer and its complement.

Figure 2:
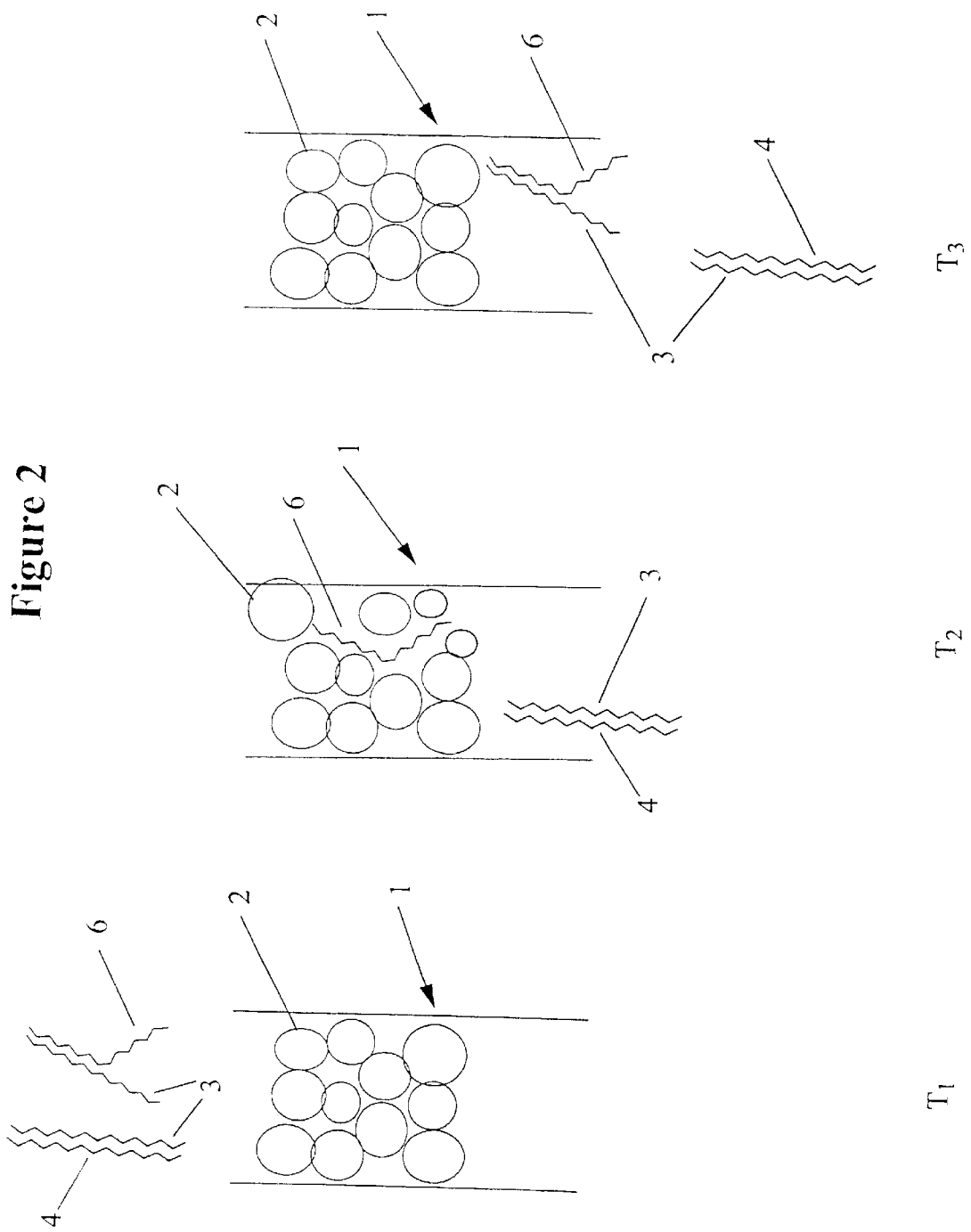
FIG. 2 is a diagram of another embodiment of the invention where the separation oligomers 3 flow through with the sample through a column 1.

FIG. 2 is a diagram of another embodiment of the invention where separation oligomers 3 flow through the column 1 with the sample. In this embodiment of the invention, the separation oligomers 3 and the sample are added to the separation medium 2 simultaneously at a time $T_1$. Thus, hybridization of target oligomers 4 and separation oligomers 3 is nearly complete upon loading onto the separation medium 2. This embodiment is particularly useful when electrophoretic techniques are used and thus, typically, the hybridized target oligomer separation oligomer pairs will travel more rapidly through the separation medium 2 due to the rigidity and increased charge. Because the system is operated at the melting temperature, the target oligomers 4 and separation oligomers 3 are continuously undergoing hybridization and dissociation at comparable rates as the sample moves through the separation medium 2. Impurity oligomers 6, on the other hand, will be attaching to and dissociating from the separation oligomers 3 at different rates than target oligomers 4. In particular, the impurity oligomers 6 will spend less time associated with the separation oligomers 3 than will the target oligomers 4. As a result, the impurity oligomers 6 will spend a larger amount of time in a single stranded state and thus remain in the column longer than the target oligomers 4. According to this embodiment, the target oligomers 4 thus emerge from the separation medium 2 prior to the impurity oligomers 6. In addition, because separation oligomers 3 will be present in solution with the target oligomers 4, many of the target oligomers 4 will be hybridized upon emergence from the separation medium 2. The target oligomers 4 can then be separated from the separation oligomers 3 using techniques well known in the art.

In yet another embodiment of the invention, the present method may be used to isolate impurities present in the sample. In this embodiment, the desired product is the impurity oligomer rather than the target oligomer. Accordingly, if the separation oligomers are attached to the separation medium, the impurity oligomers, which are now the desired entity, will move through the column more rapidly than the target oligomers, which are no longer desired. This embodiment may be used, for example, to isolate oligomers having single nucleotide polymorphism, or SNPs. SNPs are an important area of research because these can represent genetic mutations that are indicators of hereditary diseases and other disorders. In this case a sample containing predominately a naturally occurring DNA sample which has been for the most part perfectly replicated, would also contain SNPs. By using a separation oligomer that is complementary to the naturally occurring DNA, the SNPs will move through the separation medium more rapidly than the "correct" DNA and can thus be efficiently isolated. The present invention thus further represents a method of isolating SNPs not previously known or described in the art.

In addition to being useful for purification of oligomers composed in their entirety of a specific sequence of subunits, the present invention may also be used to separate oligomers having a specific subsequence of subunits within a longer sequence of subunits or oligomers having several subsequences in common. For example, it may be desirable to separate all oligomers having a particular substructure, where the substructure is a subsequence of subunits that is smaller than the entire length of the oligomer, regardless of the sequence of remaining subunits in the oligomer. Accordingly, the separation oligomers should consist of the subsequence complementary to the desired subsequence. Such separations may be less efficient than those utilizing the entire chain length due to, for example, secondary bonding within the target oligomers and steric interactions between the subsequence and other portions of the oligomer. However, the overall utility of the separation is maintained. In addition, multiple runs in such a system where each individual run utilizes a different subsequence on different separation oligomers may have utility in identifying or isolating oligomers having more than one common subsequence in common.

The present invention is useful for the purification of oligomers having any number of bases or other subunits. It will be appreciated, however, that the separation of large oligomers requires a larger amount of time or higher temperatures. Either of these changes would result in more diffusion as compared with relatively short oligomers. Thus, the oligomers which may be separated according to the invention are preferably those having less than about 200 subunits, more preferably less than about 100 subunits, and most preferably oligomers having about 50 subunits.

Although the present method may be used for purifying relatively large quantities of oligomers, the invention is particularly useful for obtaining very pure oligomers rather than obtaining a high yield of oligomer. The typical purity of oligomers obtained using the invention is at least 95% and a purity of greater than 99% may be readily obtained.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for separating target oligomers with a first subunit sequence, from impurity oligomers that do not have said first subunit sequence, the target and impurity oligomers being one of nucleic acid oligomers and analogs of nucleic acid oligomers, comprising loading a separation medium with a mixture of said target oligomers and said impurity oligomers, under conditions such that said mixture of oligomers physically moves through the separation medium;

said separation medium comprising separation oligomers comprising a subunit sequence that is complementary to said first subunit sequence;

wherein the rates of hybridization and dissociation of complementary portions of said target oligomers and said separation oligomers in said separation medium are about the same; and allowing said mixture of oligomers to move through the separation medium until said target oligomers are separated from said at least one type of the impurity oligomers.

2. The method according to claim 1, wherein the ratio of the rate of hybridization to the rate of dissociation is between about 35:65 and about 65:35.

3. The method according to claim 2, wherein the ratio is about 50:50.

4. The method according to claim 1, wherein the separation oligomers are attached to the separation medium.

5. The method according to claim 1, wherein the separation oligomers move in the separation medium, are loaded together with the mixture, and are isolable from said target oligomers.

6. The method according to claim 5, wherein the separation oligomers are end-modified to be digested by nuclease that does not digest target oligomers.

7. The method according to claim 1, wherein the separation medium comprises an electrophoretic gel.

8. The method according to claim 1, wherein the separation medium comprises a chromatographic matrix.

9. The method according to claim 8, wherein the chromatographic matrix comprises beads or fibers in a column.

10. The method according to claim 1, wherein the target oligomers are selected from the group consisting of DNA nucleotides and RNA nucleotides.

11. The method according to claim 8, conducted at about the melting temperature of the RNA nucleotides or DNA nucleotides.

12. The method according to claim 1, wherein the impurity oligomer is a single nucleotide polymorph of the target oligomer.

13. A method of separating target oligomers that are nucleic acid oligomers or analogs thereof comprising a first subunit sequence from at least one impurity oligomer that does not comprise said first subunit sequence comprising loading a separation medium with a separation oligomer comprising a subunit sequence complementary to said first subunit sequence, loading the separation medium with a mixture of oligomers comprising said target oligomers and said at least one impurity oligomer, wherein said mixture of oligomers physically moves relative to the separation medium, and allowing said mixture of oligomers to move relative to the separation medium until said target oligomers are separated from said at least one impurity oligomer;

wherein a rate of hybridization of said target oligomers and said separation oligomers is about equal to a rate of dissociation of a double stranded complex consisting of said target oligomers and said separation oligomers.

14. The method according to claim 13, wherein the ratio of the rate of hybridization to the rate of dissociation is between about 35:65 and about 65:35.

15. The method according to claim 13, wherein the ratio of the rate of hybridization to the rate of dissociation is about 50:50.

16. The method according to claim 13, wherein the separation medium and the separation oligomer are associated such that the target oligomers move relative to the separation oligomers.

17. The method according to claim 16, wherein the separation medium and the separation oligomers are associated by a chemical bond.

18. The method according to claim 13, wherein the separation oligomers move relative to the separation medium.

19. The method according to claim 13, wherein the separation medium is selected from the group consisting of electrophoretic gels and chromatographic matrices.

20. The method according to claim 13, wherein the separation oligomer is isolable from the target oligomer.

21. The method according to claim 20, wherein said separation oligomers are end-modified to be digested by a nuclease that does not digest target oligomers.

22. The method according to claim 13, further comprising reacting said separation oligomer with said separation medium.

* * * * *